US00PP37709P2

(12) United States Plant Patent
Bazak

(10) Patent No.: US PP37,709 P2
(45) Date of Patent: Sep. 22, 2026

(54) GRAPEVINE PLANT NAMED 'LATE BEAR'

(50) Latin Name: *Vitis vinifera L.*
Varietal Denomination: LATE BEAR

(71) Applicant: Bazak Agro Innovation Ltd, Carmei Yossef (IL)

(72) Inventor: Hanan Bazak, Carmei Yossef (IL)

(73) Assignee: Bazak Agro Innovation Ltd, Carmei Yossef (IL)

( * ) Notice: Subject to any disclaimer, the term of this patent is extended or adjusted under 35 U.S.C. 154(b) by 0 days.

(21) Appl. No.: 19/344,328

(22) Filed: Sep. 29, 2025

(51) Int. Cl.
*A01H 6/88* (2018.01)
*A01H 5/08* (2018.01)

(52) U.S. Cl.
USPC ..... Plt./205

(58) Field of Classification Search
USPC ..... Plt./205
CPC ..... A01H 6/88; A01H 5/08
See application file for complete search history.

(56) References Cited

U.S. PATENT DOCUMENTS

PP16,284 P2 2/2006 Ramming et al.

*Primary Examiner* — Keith O. Robinson
(74) *Attorney, Agent, or Firm* — FOLEY & LARDNER LLP

(57) ABSTRACT

A new and distinct Grapevine of *Vitis vinifera* plant named 'LATE BEAR', which has demonstrated that the combination of characteristics as herein disclosed for the new variety are firmly fixed and retained through successive generations of asexual propagation. The new variety is primarily adapted to the growing conditions in full sunlight grown in a Mediterranean, hot summer climate. The new variety is particularly characterized by a late maturing, light green, seedless very large berry.

4 Drawing Sheets

Figure 1:
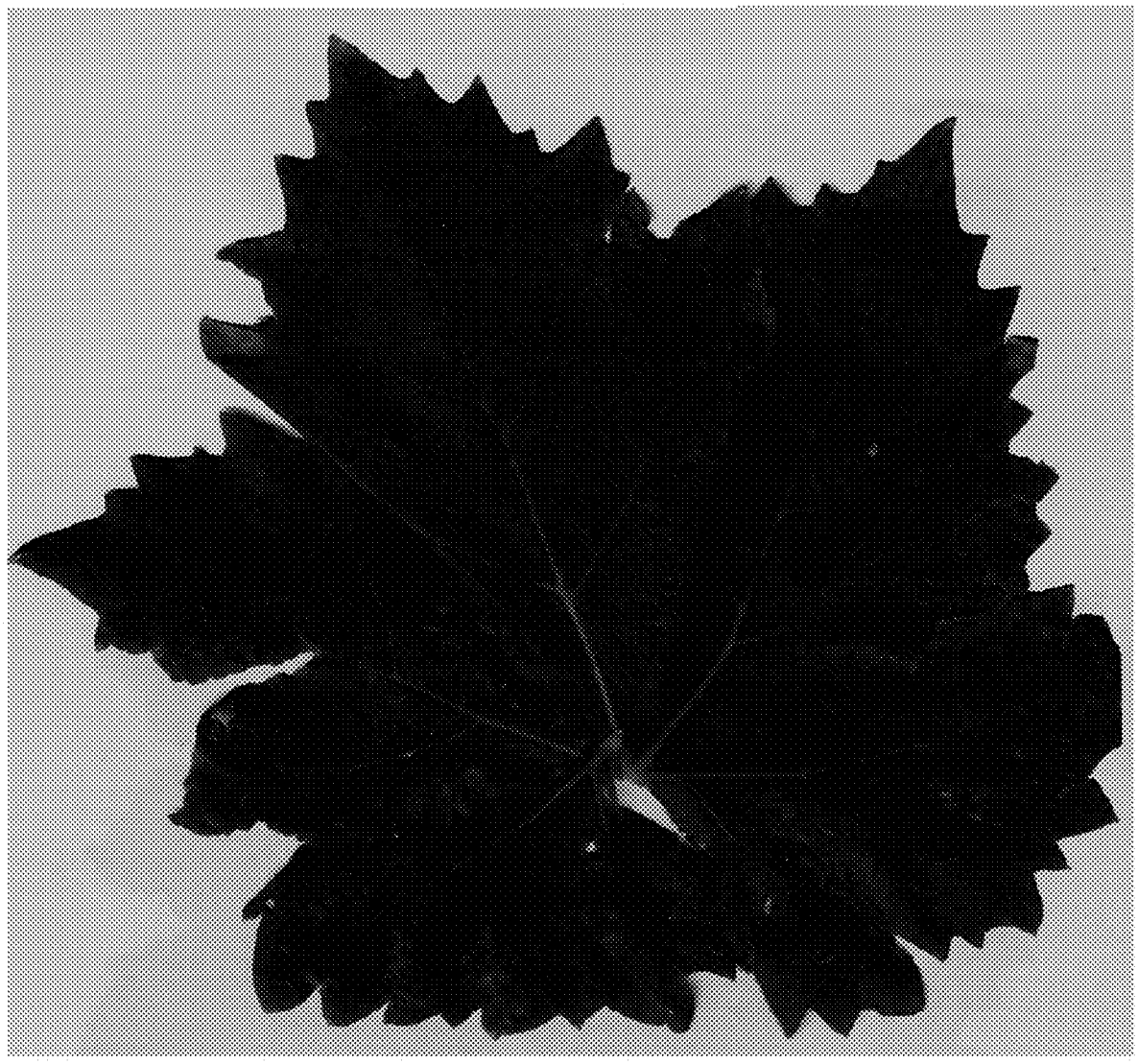
Figure 2:
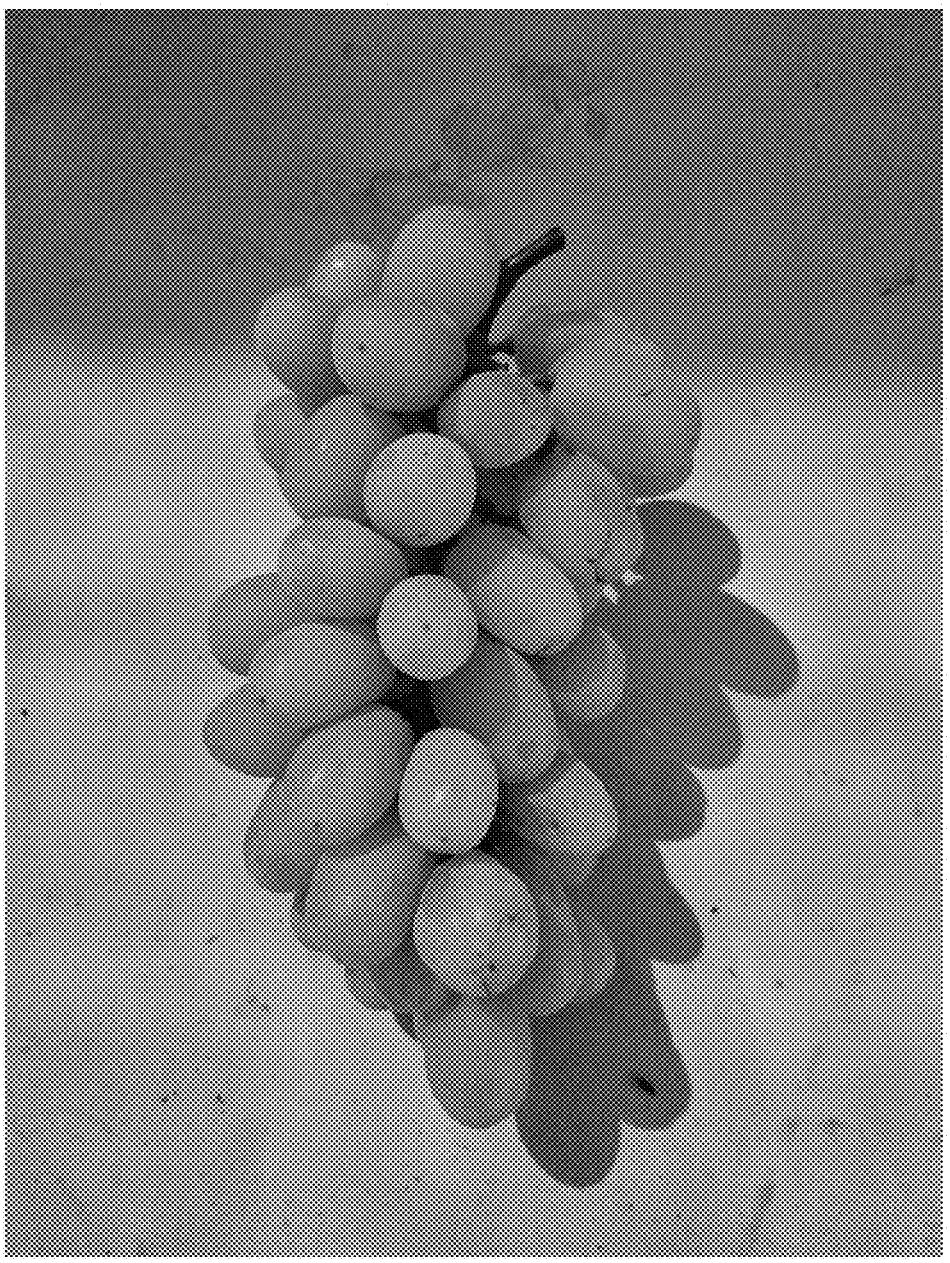
Figure 3:
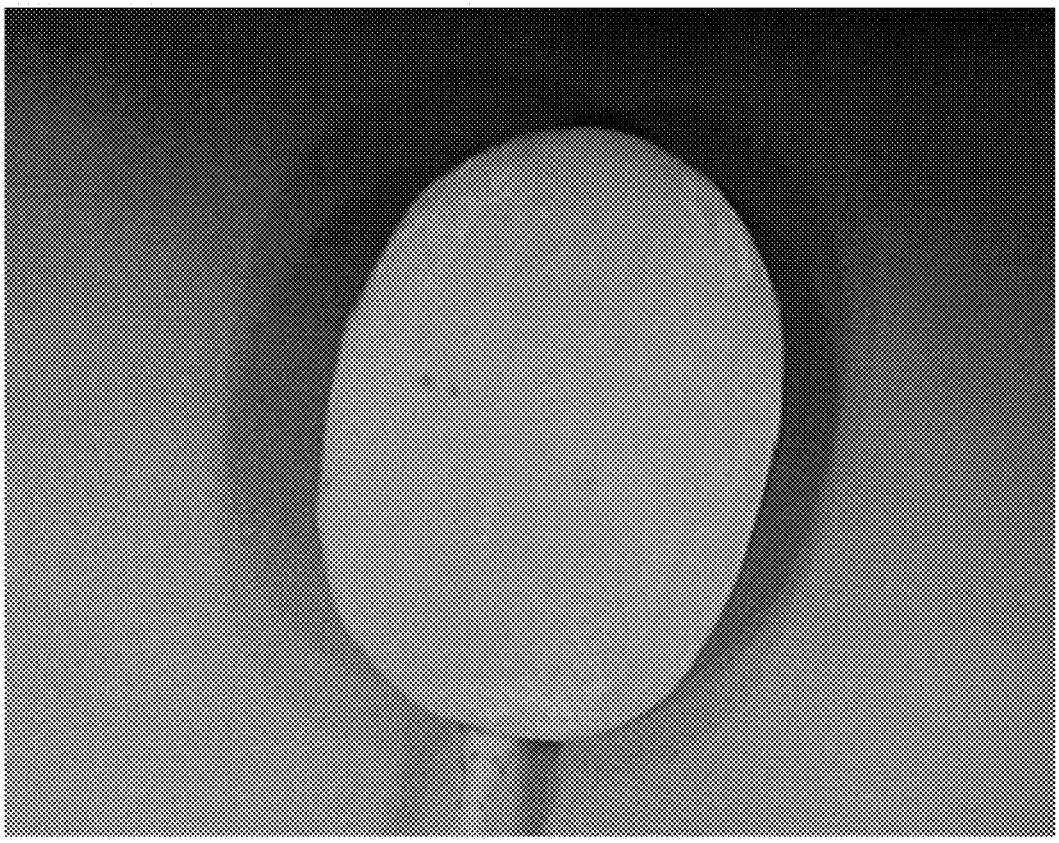
Figure 4:
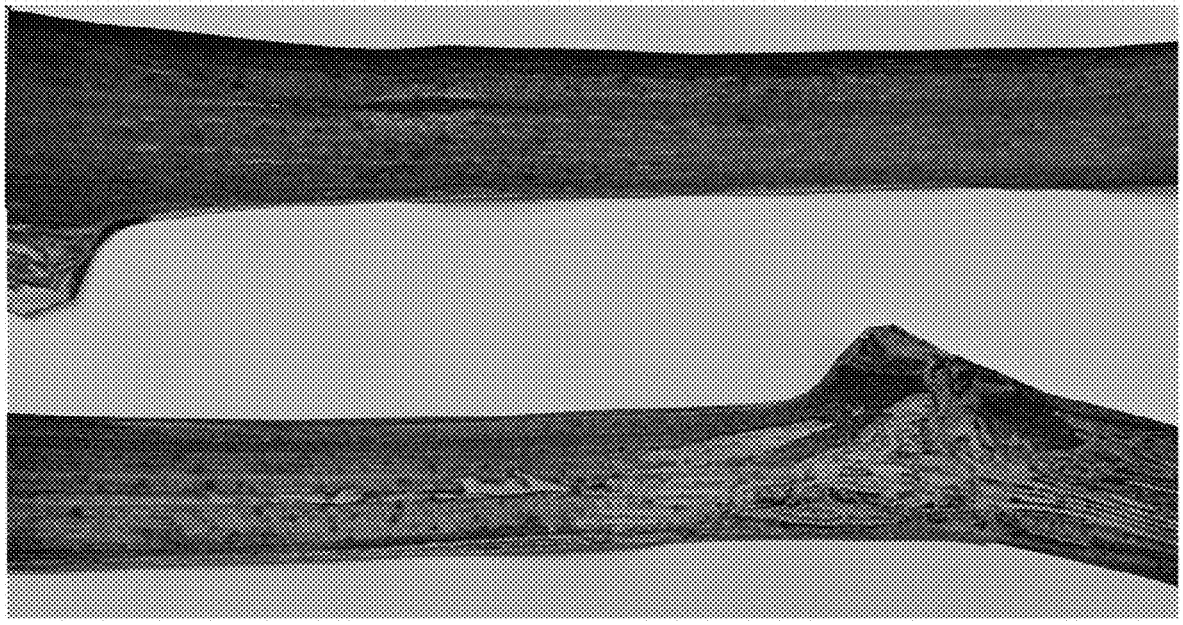

Genus and species of the plant claimed: *Vitis vinifera L.* Variety: 'LATE BEAR'.

BACKGROUND OF THE INVENTION

The present invention relates to a new and distinct variety of Grapevine plant, botanically known as *Vitis vinifera* of the *Vitaceae* family, and hereinafter referred to by the variety name 'LATE BEAR'.

The new *Vitis vinifera* variety is a product of a planned breeding program conducted by the inventor, Hanan Bazak, in Karmei Yossef, Gezer region in HaShephelah, Israel. The objective of the breeding program was to develop a new *Vitis vinifera* variety with a large, seedless, late ripening, easy detachable berry with firm flesh, excellent taste and with low susceptibility to Grape Sour Rot.

The new *Vitis vinifera* variety originated from a cross made by the inventor in 2012 in Karmei Yossef, Gezer region in HaShephelah, Israel. The female or seed parent is the *Vitis vinifera* designated 'H 4795' (unpatented). The male or pollen parent is the *Vitis vinifera* designated 'H 6367', (unpatented). The new *Vitis vinifera* 'LATE BEAR' was observed and selected by the inventor within the progeny of the stated cross in a controlled environment in 2012 in Karmei Yossef, Gezer region in HaShephelah, Israel.

Asexual propagation of the new *Vitis vinifera* variety by rooting of cuttings was first performed in 2018 in Karmei Yossef, Gezer region in HaShephelah, Israel., and has demonstrated that the combination of characteristics as herein disclosed for the new variety are firmly fixed and retained through successive generations of asexual propagation. The new variety propagates true-to-type.

BRIEF DESCRIPTION OF THE INVENTION

The following traits have been repeatedly observed and are determined to be characteristics of 'LATE BEAR' which in combination distinguish this Grapevine plant as a new, unique and distinct variety:

1. Berry ripening time: late-season.
2. Berry shape: long obovoid.
3. Berry skin color: greenish yellow.
4. Berry flesh flavor: none.
5. Berry seed formation: mainly seedless with some rudimentary seeds.

In comparison to the parental varieties, Female or seed parent 'H 4795' (unpatented) and the Male or pollen parent 'H 6367' (unpatented), 'LATE BEAR' differs primarily in the traits listed in Table 1.

TABLE 1

Comparison with parent varieties

| Characteristic | New Variety 'LATE BEAR' | Female Parent 'H 4795' (unpatented) | Male Parent 'H 6367' (unpatented) |
|---|---|---|---|
| Berry ripening time | late | Mid-season to late | Very late |
| Berry skin color | Green-yellow | Green-yellow | Green-yellow |
| Berry shape | Long ovoid | ovoid | Ovoid to spherical |

Of the many well-known commercial varieties known to the present inventor, the most similar in comparison to the new *Vitis vinifera* 'LATE BEAR' is *Vitis vinifera*

'AUTUMN KING' (U.S. Plant Pat. No. 16,284 P2) which differs from the new Grapevine 'LATE BEAR' in the characteristics described in Table 2:

TABLE 2

| Comparison with a well-known commercial variety | | |
|---|---|---|
| Characteristic | New Variety 'LATE BEAR' | Comparison Variety 'AUTUMN KING' (U.S. Plant Pat. No. 16,284 P2) |
| Berry ripening time | Late season | Late season |
| Berry shape | Long ovoid | Cylindrical to ovoid |
| Berry skin color | Yellow green | Pale green |
| Berry flesh structure | firm | firm |

BRIEF DESCRIPTION OF THE PHOTOGRAPHS

The accompanying photographs illustrate the overall appearance of the new *Vitis vinifera* variety 'LATE BEAR' showing the colors as true as is reasonably possible with colored reproductions of this type.

Colors in the photographs may differ slightly from the color values cited in the detailed morphological description, which accurately describes the color of 'LATE BEAR'.

Photograph 1 —shows a typical leaf of 'LATE BEAR'.

Photograph 2 —shows a typical fruit bunch of 'LATE BEAR'.

Photograph 3 —shows a typical berry of 'LATE BEAR'.

Photograph 4 —shows a typical woody shoot of 'LATE BEAR'.

DETAILED MORPHOLOGICAAL DESCRIPTION

The new *Vitis vinifera* 'LATE BEAR' has not been observed under all possible environmental conditions. The phenotype of the new variety may vary with variations in environment such as temperature, light intensity, day length, soil or pruning without any change in the genotype of the Grapevine plant.

The aforementioned photographs, together with the following observations, measurements and values describe plants/trees of 'LATE BEAR' as grown in the vineyard in Karmei Yossef, Gezer region in HaShephelah, Israel—under conditions which closely approximate those generally used in commercial practice.

Unless otherwise stated, the detailed morphological description includes observations, measurements and values taken from 2023 to 2025 and based on 10 five-year-old 'LATE BEAR' plants grown in the vineyard in Karmei Yossef, Gezer region in HaShephelah, Israel. Quantified measurements are expressed as an average or a range of measurements taken from a number of plants of 'LATE BEAR'. The measurements of any individual plant, or any group of plants, of the new variety may vary from the stated average or range.

Color references are made to The Royal Horticultural Society Colour Chart (R.H.S.), edition 1986, except where general colors of ordinary significance are used. Color values were taken under daylight conditions in full sunlight in location, region, Israel.

All of the plants of 'LATE BEAR', insofar as they have been observed, have been consistent in all the characteristics described below.

Classification:

*Botanical.—Vitis vinifera.*

Parentage:

*Female or Seed Parent.—Vitis vinifera* 'H 4795' (unpatented).

*Male or Pollen Parent.—Vitis vinifera* H 6367 (unpatented).

Propagation: Rooted cuttings.

Growing conditions:

*Light intensities.*—Full sunlight.

*Temperature.*—During day, grown in range of 10° C. to 35° C., and during the night grow in range of 0° C. to 25° C.

*Karmei Yosef Climate Summary.* —Located at an elevation of 238.79 meters (783.43 feet) above sea level, Karmei Yosef has a Mediterranean, hot summer climate (Classification. Csa). The district's yearly temperature is 23.04° C. (73.47° F.) and it is 0.35% higher than Israel's averages. Karmei Yosef typically receives about 16.8 millimetres (0.66 inches) of precipitation and has 40.43 rainy days (11.08% of the time) annually. Karmei Yosef, Central District, Israel Climate Weather: 16.73° C./62.11° F, Wind SW at 2.57 km/h, 61% Humidity, 0.15% chance of rain.

TABLE 3

| Karmei Yosef Climate Summary January-June | | | |
|---|---|---|---|
| Kamei Yossef yearly average of temperature and precipitation | JAN | FEB | MAR |
| Daily mean temperature | 12° C. (53° F.) | 13° C. (55° F.) | 15° C. (59° F.) |
| Average precipitation mm (inches) | 48 (1.9) | 44 (1.7) | 39 (1.5) |
| Kamei Yossef yearly average of temperature and precipitation | APR | MAY | JUN |
| Daily mean temperature | 19° C. (66° F.) | 23° C. (74° F.) | 25° C. (77° F.) |
| Average precipitation mm (inches) | 19 (0.8) | 7 (0.3) | 2 (0.1) |

TABLE 4

| Karmei Yosef Climate Summary July-December | | | |
|---|---|---|---|
| Kamei Yossef yearly average of temperature and precipitation | JUL | AUG | SEP |
| Daily mean temperature | 27° C. (82° F.) | 28° C. (82° F.) | 26° C. (80° F.) |
| Average precipitation mm (inches) | 1 (0.0) | 1 (0.0) | 1 (0.0) |

TABLE 4-continued

| Karmei Yosef Climate Summary July-December | | | |
|---|---|---|---|
| Kamei Yossef yearly average of temperature and precipitation | OCT | NOV | DEC |
| Daily mean temperature | 23° C. (74° F.) | 19° C. (66° F.) | 15° C. (59° F.) |
| Average precipitation mm (inches) | 14 (0.6) | 25 (1.0) | 33 (1.3) |

Fertilization: A balanced fertilizer with a level of NPK 25.7.30 from bud burst in January till February.

Growth regulators: Dormex to stimulate bud wakening and gibberellin to enlarge berry size.

Plus microelements: 1.5 L. in each 5 $m^3$ of water.

Pruning: As in commercial practice: 4 long young shoots each with 12 eyes.

The size and overall shape of Grapevine plants essentially depend on pruning and spacing. 'LATE BEAR' was pruned, creating a plant which is trailing horizontally with three, four or five main vines. When the plants are freely grown, the size and the shape assumed by the plants are typical of *Vitis vinifera.*

Plant:

*Age.*—Observed plants were 5 years old.

*Time of bud burst.*—Mid-season to late.

*Maturity.*—Ripe for commercial harvesting; about the end of September.

*Young shoot.*—Openness of tip: half open. Density of prostrate hairs on tip: absent or very sparse. Anthocyanin coloration of prostrate hairs on tip: absent or very sparse. Color: green-RHS 145 A.

*Young leaf.*—Color of upper side of leaf blade: light green-RHS 145 A. Color of lower side of leaf blade: light green-RHS 144 C. Anthocyanin coloration: absent. Density of hairs between main veins on lower side of blade: absent or very sparse. Glossiness of upper side: strong. Glossiness of lower side: medium. Length of internode: up to 4-8 cm.

*Shoot.*—Color of dorsal side of internode: medium green RHS 144 A. Color of ventral side of internode: light green RHS 144 B. Color of dorsal side of node: medium green RHS 144 A. Color of ventral side of node: light green RHS 144 B. Density of erect hairs on internodes: absent or very sparse. Consecutive tendrils: at all modes. Length of tendril: up to 10 cm.

*Inflorescence.*—Length: about 15-22 cm. No. of side branches: about 9-13. Attitude of side branches: semi-upright. Length of longest side branch: about 5-6 cm. Thickness of main axis: about 3 mm. Green color of main axis: light yellow green-RHS 146 D. Anthocyanin coloration of main axis: absent. Pubescence of main axis: absent.

*Flower.*—Sexual organs: fully developed stamens and fully developed gynoecium.

*Full bloom.*—Mid-April.

*Pedicel.*—Length: about 1 mm. Thickness: about 0.5 mm. Green color: light green-RHS 146 D. Pubescence: absent.

*Stamen.*—Length of filament: about 2-3 mm. Thickness of filament: minuscule. Pubescence of filament: absent. Surface: smooth. Color: light green-RHS 145 C.

*Anther.*—Shape: transverse elliptic elongated. Length: minuscule. Color: Light green-RHS 145 C.

*Pollen.*—Amount: abundant. Color: yellow-RHS 150 B.

*Ovary.*—Shape: elliptic. Color: green-RHS 144 A. Length: about 1-2 mm. Diameter: about 1 mm. Surface: smooth.

*Style.*—Length: minuscule.

*Stigma.*—Size: minuscule. Color: yellow — RHS 150 B.

*Mature leaf.*—Size of blade: small to medium. Blade length: about 11-14 cm. Blade width: about 13-15 cm. General shape of blade: wedge shape. Green color of upper side: medium green RHS 144 A. Green color of lower side: light green RHS 144 B. Glossiness of upper side: medium. Glossiness of lower side: weak. Profile in cross section: flat. Blistering of upper side: absent. Number of lobes: 5. Central lobe length: about 6 cm. Central lobe width: about 8 cm. Upper lateral lobe length: about 5 cm. Upper lateral lobe width: about 8 cm. Pubescence of veins on upper side: absent or very sparse. Pubescence of veins on lower side: absent or very sparse. Green color of veins on upper side: medium to dark green-RHS 143 A. Green color of veins on lower side: medium green-RHS 143 B. Anthocyanin coloration of veins on upper side: absent. Anthocyanin coloration of veins on lower side: absent. Depth of upper lateral sinuses: very shallow. Arrangement of lobes of petiole sinus: half overlapping. Petiole sinus limited by veins: none. Length of distal tooth: about 2 mm. Width of distal tooth: about 4 mm. Ratio length/width of distal tooth: 0.5. Shape of teeth: straight on both sides. Anthocyanin coloration of main veins on upper side of blade: absent or very sparse. Density of hairs between veins on upper side of blade: absent or very sparse. Density of hairs between veins on lower side of blade: absent or very sparse. Length of petiole compared to middle vein: moderately shorter.

*Petiole.*—Length: about 6 cm. Thickness: about 2 mm. Green color of upper side: dark green-RHS 146 A. Anthocyanin coloration of upper side: absent, or partly medium strong. Anthocyanin coloration of lower side: absent or very sparse. Green color of lower side: very light green-RHS 144 D. Pubescence: absent or very sparse.

*Fruit.*—Time of beginning of berry ripening: late to very late.

*Bunch.*—Length (peduncle excluded): 13-23 cm. Width (peduncle excluded): 9-11 cm. General shape (peduncle excluded): cylindrical. Weight (peduncle excluded): 1.600-13.00 g. Density: dense. Length of peduncle: 2-3 cm.

*Berry.*—Length: 22-28 mm. Diameter: about 30 mm. Shape: obolid, weight 22-30 g. Color of skin (without bloom): very light green-RHS 144 D. Ease of pedicel detachment: moderately easy. Length of pedicel: 2 mm. Thickness of pedicel: less than 1 mm.

Color of pedicel: very light green-RHS 144 D. Thickness of skin: thick. Flesh anthocyanin coloration: absent. Firmness of flesh: very firm. Juiciness of flesh: juicy. Total soluble solids: 16-20° Bx. Acidity: 0.4-0.8 pH. Particular flavour: none. Formation of seeds: rudimentary.

*Woody shoot.*—Main color (without bloom): medium greyed orange — RHS 168 A. Relief of surface: smooth.

Disease resistance: Resistant to Grape Sour Rot.

Pest resistance: No atypical resistance has been noted.

Usage: Table grape.

Shipping quality: Mostly packed in 5-10 cartons.

Storage life and productivity: The grapes can be easily stored in the refrigerator for over a month. Productivity is 50-60 kg for plants in average conditions and on adult plants.

I claim:

1. A new and distinct Grapevine variety of *Vitis vinifera* plant named 'LATE BEAR', as illustrated and described herein.

* * * * *